United States Patent [19]

Singh et al.

[11] Patent Number: 5,892,138
[45] Date of Patent: Apr. 6, 1999

[54] PROCESS FOR THE PREPARATION OF HALOCUMENES

[75] Inventors: Anand Pal Singh; Sushama Mohan Kale, both of Maharashtra, India

[73] Assignee: Council of Scientific & Industrial Research, New Delhi, India

[21] Appl. No.: 956,578

[22] Filed: Oct. 23, 1997

[30] Foreign Application Priority Data

Feb. 21, 1997 [IN] India ................................ 422/DEL/97

[51] Int. Cl.$^6$ .................................................. C07C 22/00
[52] U.S. Cl. ............................................ 570/208; 570/206
[58] Field of Search ..................................... 570/206, 208

[56] References Cited

U.S. PATENT DOCUMENTS 4,792,644 12/1988 Hironaka et al. ....................... 570/206
4,849,560 7/1989 Sekizawa et al. ....................... 570/208

FOREIGN PATENT DOCUMENTS 5140013 6/1993 Japan ..................................... 570/208

*Primary Examiner*—Alan Siegel
*Attorney, Agent, or Firm*—Dickinson Wright PLLC

[57] ABSTRACT

A process for the preparation of 4-halocumenes is disclosed wherein the halogen in the halocumene is chlorine, bromine, or iodine, the process including the step of reacting cumene with a halogenating agent in a liquid phase in the presence of a solvent, an aliphatic carboxylic acid component, and a zeolite catalyst.

12 Claims, No Drawings

PROCESS FOR THE PREPARATION OF HALOCUMENES

FIELD OF INVENTION

The present invention relates to an improved process for the preparation of halocumenes. More particularly, it relates to a process for the selective preparation of 4-halocumenes represented by formula 1 in the drawing accompanying this specification, wherein, R=Cl or Br or I from cumene with halogenating agents such as $Cl_2$, $Br_2$, ICl in presence of a zeolite catalyst in combination with an aliphatic carboxylic acid.

4-halocumenes are useful for the production of intermediates for agrochemicals and pharmaceuticals.

BACKGROUND OF INVENTION

In the prior art, 4-halocumenes are prepared by various methods described herein below:

As a process for the liquid phase chlorination of cumene, it has been common to conduct chlorination in the presence of Lewis acid catalyst such as ferric chloride or aluminium chloride by means of a chlorinating agent such as chlorine gas. However, such a process produces 2-chlorocumene as a major product and polychlorinated derivatives as by-products whereby it is difficult to produce 4-chlorocumene in good selectivity as high as at least 90%. Under these circumstances, there have been various researches for the development of catalyst to improve the selectivity for 4-chlorocumene.

In one method, chlorination of cumene was carried out using ferric chloride and chlorine gas which gives a mixture of cumene 1.8%, 2-chlorocumene 41.8%, 3-chlorocumene 1%, 4-chlorocumene 40.8% and polychlorinated cumenes 15% (Jpn. Kokai 5959,434 [8453,434]).

In another method, chlorination of cumene was carried out with $Cl_2$ in $CCl_4$ in the presence of chemically modified silica catalyst for 2 h. In this case, the para/ortho ratios were slightly higher than those with $FeCl_3$ (Chem. Lett. 11(1980) 1423).

4-chlorocumene is also made by ring cumene with chlorine gas in the presence of Fe and FeS at 50° C. After 2 h, the reaction mixture contained cumene 10.6%, 2-chlorocumene 28.8%, 3-chlorocumene 0.8%, 4-chlorocumene 56.6% and polychlorinated cumenes 3.3%. (Jpn. Kokai Tokkyo Koho JP 59,53,433 [84 53,433](Cl. C07 C25/02).

In another known method, chlorination of cumene over silica gel catalyst treated with nitrobenzene derivatives gives a mixture of 2-chlorocumene and 4-chlorocumene in a ratio of 1:2 ( Jpn. Kokai Tokkyo Koho JP 58 81, 443).

In another method, 4-chlorocumene is obtained in a selectivity of 75% by reacting cumene with chlorine by means of a $SbCl_3$ modified catalyst (Jpn. Kokai Tokkyo Koho JP 60,125,251[85,125,251]).

In the prior art, bromination of cumene is achieved using molecular bromine adsorbed on the surface of alumina without any solvent (Synth. Commn. 1992, 22(8), 1095). This method is disadvantageous since it is an adsorptive method.

In another method, cumene was brominated with N-bromosuccinimide (Ind. J. Chem. 1983, 22 B, 592).

The iodination of cumene was carried out by using $I_2$—$Hg(NO_3)_2$ as an iodinating agent. The yields for iodocumenes and the selectivity for para-iodocumene were found to be 92 wt. % and 73%, respectively (Tetrahedron, 1994, 50(17), 5139).

However, these conventional methods are not satisfactory as a process for the production of 4-halocumenes because the selectivity for 4halocumenes is low (>75%) in each case.

In view of the above mentioned low selectivity for 4-halocumenes in the prior art processes, it was found desirable during the course of the research work leading to the present invention to develop an improved process for the production of 4-halocumene in high selectivity from the halogenation of cumene using zeolite catalyst.

SUMMARY OF INVENTION

The object of the present invention is to provide an improved process for the preparation of halo-cumenes, particularly, 4-halocumenes in high selectivity by liquid phase chlorination of cumene with chlorine gas using a composite catalyst material, zeolite and an aliphatic chloro carboxylic acid component.

Accordingly, the present invention provides an improved process for the preparation of halocumenes, which comprises reacting cumene with halogenating agent in a liquid phase in the presence of an aliphatic carboxylic acid and a microporous zeolite catalyst composite material having molar compositions as follows: $M_{2/n}O: Al_2O_3:zSiO_2$ (where M is an alkali or alkaline earth metal with valency n and z is between 2 to 500) having $SiO_2/Al_2O_3$ molar ratio varying from 2 to 10 and a pore size of 6 to 10 Å, at a temperature in the range of 5° and 150° C. at autogenous pressure for a period in the range of 1 to 20 hrs. and recovering the halocumenes of formula I of the drawing accompanying this specification wherein R=Cl, Br or I from the reaction mixture by the conventional methods.

In a preferred embodiment of the, invention, solvent used is such as dichloromethane, carbon tetrachloride, 1,2-dichloroethane, 1,1,1-trichloroethane, 1,1,2,2-tetrachloroethane and sulfolane.

In one of the embodiments of the present invention, the catalyst composite material employed, may be such as a microporous crystalline aluminosilicate, zeolite K-L or zeolite H-beta type, H-ZSM-5, H-ZSM-12 or H-mordenite.

In still another embodiment of the invention, the halogenating agent used may be such as $Cl_2$, $Br_2$, ICl.

In another embodiment of the invention proportion of cumene, solvent, aliphatic carboxylic acid or derivatives, zeolite catalyst type and halogenating agent used ranges from 0.01 to 1 mol, 0 to 500 ml, 0 to 50 wt. %, 0.1 to 900 g/mol cumene and 0.001 to 500 mol/h, respectively.

In the process of the present invention, it is essential to use the catalyst, a combination of an aliphatic carboxylic acid component and a zeolite (aluminosilicate) having a $SiO_2/Al_2O_3$ molar ratio of from 2 to 10 and a pore size of from 6 to 10 Å. When a zeolite with a $SiO_2/Al_2O_3$ molar ratio or pore size being outside the above mentioned range is used, the selectivity for the above mentioned product will be substantially poor.

A typical representative of the zeolite which satisfies the above mentioned conditions, is L-type zeolite, which is a crystalline aluminosilicate having a $SiO_2/Al_2O_3$ molar ratio of from 2 to 10 and a pore size of from about 7 to 10 Å.[Zeolites, 10(1990),598]. Further, the ion-exchangeable cations contained in such zeolite are usually sodium or potassium, but may further include other cations of the group IA, IIA, IIIA or VA of the periodic table. The cations may be of the same type or of two or more different types.

In the process of the present invention, it is essential to use a solvent. When a solvent is used in the process of the present invention, the selectivity for the 4-halocumenes will be higher. The solvents which give the higher selectivity for 4-halocumenes are: hydrocarbons such as dichloromethane, carbon tetrachloride, 1,2-dichloroethane, 1,1,1-trichloroethane and 1,1,2,2-tetrachloroethane and sulfolane. A typical representative of the solvent which gives the highest selectivity for 4-halocumenes in the presence of a zeolite and an aliphatic carboxylic acid is 1,2-dichloroethane.

According to the process of the present invention, it is possible to selectively and efficiently halogenate the para-position of cumene while suppressing the halogenation at the ortho-position and to minimize the formation of by-products such as side-chain halogenated products or polyhalogenated products, whereby highly useful 4-halocumenes can be obtained in good selectivity.

The term "aliphatic chloro carboxylic acid component" includes an aliphatic carboxylic acid and its derivatives such as halide anhydride or metal salts of an aliphatic carboxylic acid. As the aliphatic carboxylic acid, there may be mentioned acetic acid, propionic acid, isovaleric acid, monochloroacetic acid, monobromoacetic acid, dichloroacetic acid, trichloroacetic acid, α-chloropropionic acid, β-chloropropionic acid, difluoroacetic acid, trifluoroacetic acid, pentafluoropropionic acid or β-chlorotetrafluoropropionic acid which may be substituted or unsubstituted. The metal salt may be a sodium or potassium or barium salt of an aliphatic carboxylic acid. The halide may be a chloride or a bromide of an aliphatic carboxylic acid. Among them, aliphatic carboxylic acid and their metal salts are preferred. Among them, sodium salt or potassium salts are further preferred.

The reactants and solvents which are employed in the process of the present invention are desired to be in high purity. In the present invention, the zeolite and the aliphatic carboxylic acid component may be added to the reactant in a manner as follows: 1) The zeolite and the aliphatic carboxylic acid component may be combined and added to the reactants prior to the halogenation, 2) The zeolite and the aliphatic carboxylic acid component may be added simultaneously to the reaction system during the reaction. 3) The zeolite is suspended in a solvent, a predetermined amount of the aliphatic carboxylic acid component is added thereto, 4) The zeolite is suspended in the reactant and solvent, then a predetermined amount of the aliphatic carboxylic acid component is added thereto and the mixture is stirred at a temperature lower than the boiling point, preferably from 20° to 150° C., followed by the halogenation.

Furthermore, according to the process of the present invention, the operation of the reaction and the subsequent after treatment is simple and the catalyst can be reused.

In a feature of the process of the present invention is the use of non-hazardous aluminosilicate catalyst.

Another feature of the process of the present invention is that it does not pose risk of explosion.

Thus, the process of the present invention is suitable as an industrial process for the production of 4-halocumenes in high selectivity.

DETAILED DESCRIPTION

The present invention is described in further detail with reference to examples which are illustrative only and should not be construed to limit the scope of the invention in any manner.

EXAMPLE-1

This example describes the preparation of the catalyst composite material, aluminosilicate (zeolite L). In a typical preparation, 4.85 g aluminium source was dissolved in a solution of 4.8 g sodium hydroxide, 20.16 g potassium hydroxide and 105 g of water to yield solution A. 37.32 g fumed silica was added slowly, with vigorous stirring to solution A. The gel so obtained was transferred into a stainless steel autoclave and the autoclave was capped tightly and put in an oven thermostated at the desired temperature for 4.5 days. Then the autoclave was removed from the oven and the crystallization was terminated by quenching the autoclave reaction with cold water. After cooling, the autoclave was opened, the contents were filtered, washed thoroughly and dried at 120° C. for 8 hrs. The X-ray diffraction and framework IR data of the so obtained material correspond to those given in Table 1 and Table 2, respectively.

TABLE 1

| Aluminosilicate, zeolite K-L | |
|---|---|
| Interplanar distance d.A°. | Relative intensity |
| 15.93 ± .05 | 100 |
| 8.20 ± .05 | 6.3 |
| 7.52 ± .05 | 29.2 |
| 6.02 ± .05 | 22.2 |
| 5.82 ± .05 | 17.5 |
| 4.80 ± .04 | 24.5 |
| 3.82 ± .04 | 28.2 |
| 3.66 ± .04 | 22.0 |
| 3.48 ± .03 | 14.8 |
| 3.28 ± .03 | 16.1 |
| 3.18 ± .03 | 28.4 |
| 3.06 ± .03 | 22.4 |
| 2.81 ± .03 | 35.8 |
| 2.85 ± .03 | 16.1 |

TABLE 2

| Inferred spectroscopic data of catalyst composite material alumiosilicate zeolite K-L. | |
|---|---|
| Frequency ($cm^{-1}$) | Relative intensity |
| 1150 | vs |
| 1080 | vs |
| 1020 | vs |
| 770 | m |
| 720 | m |
| 608 | m |
| 438 | sh |

The chemical composition of the catalyst material in the anhydrous state was:

$K_2O: Al_2O_3: 6.32 SiO_2$

EXAMPLE-2

This example illustrates the procedure for the conversion of cumene to 2-chlorocumene, 3-chlorocumene, 4-chlorocumene, α-chlorocumene and polychlorinated cumenes. The reaction was carried out in a three necked flask (250 ml), one neck was fitted with a condenser, another with a thermometer and the third with a rubber septum. 60 g cumene and 2 g catalyst composite material, zeolite K-L as set out in example 1, were taken in the flask. 0.652 g mono-chloroacetic acid was added thereto. The reaction mixture is stirred and heated upto 70° C. in the presence of nitrogen gas. Then, chlorine gas was supplied at a rate of 0.33 mol/h for three hours to conduct the reaction while maintaining the reaction temperature at 70° C. After the completion of the reaction, the reaction mixture cooled to room temperature and analyzed by gas-chromatography. The results are recorded in Table 3.

TABLE 3

Chlorination of cumene over catalyst composite material, aluminosilicate zeolite K-L after 3 hours.

| | |
|---|---|
| Cumene Conversion (wt. %) | 92.3 |
| Product yields (wt. %) | |
| 2-chlorocumene | 7.85 |
| 3-chlorocumene | 1.64 |
| 4-chlorocumene | 75.55 |
| α-chlorocumene | 0.78 |
| Polychlorinated cumenes | 6.53 |
| selectivity to para-chlorocumene in chlorocumenes | 88.8 |

EXAMPLE-3

This example illustrates the effect of reaction time on the conversion of cumene to 2-chlorocumene, 3-chlorocumene, 4-chlorocumene, α-chlorocumene and polychlorinated cumenes. The reaction was carried out in a three necked flask (250 ml), one neck was fitted with a condenser, another with a thermometer and the third with a rubber septum. 60 g cumene and 2 g catalyst composite material, zeolite K-L as set out in example 1, were taken in the flask. 0.652 g mono-chloroacetic acid was added thereto. The reaction mixture is stirred and heated upto 70° C. in the presence of nitrogen gas. Then, chlorine gas was supplied at a rate of 0.33 mol/h for three hours to conduct the reaction while maintaining the reaction temperature at 70° C. After the completion of the reaction, the reaction mixture cooled to room temperature and analyzed by gas-chromatography. The results are recorded in Table 4.

TABLE 4

Effect of reaction time on the conversion and selectivity in the chlorination of cumene over catalyst composite material aluminosilicate, zeolite K-L.

| Reaction time (h) | 1 | 2 | 3 |
|---|---|---|---|
| Cumene conversion (wt. %) | 34.20 | 66.60 | 92.30 |
| Product yields (wt. %) | | | |
| 2-chlorocumene | 2.60 | 5.30 | 7.85 |
| 3-chlorocumene | 0.62 | 1.20 | 1.64 |
| 4-chlorocumene | 30.73 | 58.00 | 75.55 |
| α-chlorocumene | 0.18 | 0.50 | 0.78 |
| Polychorinated cumenes | 0.07 | 1.60 | 6.53 |
| Selectivity to para-chlorocumene in chlorocumenes (%) | 90.51 | 89.90 | 88.80 |

EXAMPLE-4

This example illustrates the effect of the reaction temperature on the yield and selectivity of 4-chlorocumene. The reaction was carried out in a three necked flask (250 ml), one neck was fitted with a condenser, another with a thermometer and the third with a rubber septum. 60 g cumene and 2 g catalyst composite material, zeolite K-L as set out in example 1, were taken in the flask. 0.652 g mono-chloroacetic acid was added thereto. The reaction mixture is stirred and heated at different temperatures in the presence of nitrogen gas. Then, chlorine gas was supplied at a rate of 0.33 mol/h to conduct the reaction. After the completion of the reaction, the reaction mixture cooled to room temperature and analyzed by gas-chromatography. The results are recorded in Table 5.

TABLE 5

Effect of reaction temperature on the conversion and selectivity in the chlorination of cumene over catalyst composite material, aluminosilicate, zeolite K-L.

| | | |
|---|---|---|
| Reaction temperature (°C.) | 110 | 139 |
| Reaction time ( h) | 3 | 2.5 |
| Cumene conversion (wt. %) | 92.3 | 76.6 |
| Product yields (wt. %) | | |
| 2-chlorocumene | 7.85 | 11.4 |
| 3-chlorocumene | 1.64 | 2.1 |
| 4-chlorocumene | 75.55 | 58.6 |
| α-chlorocumene | 0.78 | 1.8 |
| Polychlorinated cumenes | 6.53 | 2.7 |
| Selectivity to para-chlorocumene in chlorocumenes (%) | 88.8 | 81.3 |

EXAMPLE-5

In this example, the influence of the solvent ( 1,2-dichloroethane) is demonstrated on the conversion of cumene to 2-chlorocumene, 3-chlorocumene, 4-chlorocumene, α-chlorocumene and polychlorinated cumenes. 40 g of cumene and 150 ml of 1,2-dichloroethane and 1 g of catalyst composite material, zeolite K-L, as set out in example 1 were taken for the reaction in a three necked flask. 0.652 g mono-chloroacetic acid was added thereto. The reaction mixture was stirred and heated upto 50° C. in the presence of nitrogen gas. Then, chlorine gas was supplied at a rate of 0.33 mol/h for two hours to conduct the reaction while maintaining the reaction temperature at 50° C. After the completion of the reaction, the reaction mixture was cooled to the room temperature and analyzed with gas-chromatography. The results are recorded in Table 6.

TABLE 6

Effect of solvent (1,2-dichloroethane) on the selectivity in the chlorination of cumene over catalyst composite material, aluminosilicate, zeolite K-L.

| | |
|---|---|
| Cumene conversion (wt. %) | 68.8 |
| Product yields (wt. %) | |
| 2-chlorocumene | 2.85 |
| 3-chlorocumene | 0.81 |
| 4-chlorocumene | 64.51 |
| α-chlorocumene | 0.00 |
| Polychlorinated cumenes | 0.58 |
| selectivity to para-chlorocumene in chlorocumenes | 94.63 |

EXAMPLE-6

This example illustrates the effect of the reaction time on the conversion of cumene to 2-chlorocumene, 3-chlorocumene, 4-chlorocumene, α-chlorocumene and polychlorinated cumenes in the presence of solvent 1,2-dichloroethane. 40 g of cumene and 150 ml of 1,2-dichloroethane and 1 g of catalyst composite material, zeolite K-L, as set out in example 1 were taken for the reaction in a three necked flask. 0.652 g mono-chloroacetic acid was added thereto. The reaction mixture was stirred and heated upto 50° C. in the presence of nitrogen gas. Then, chlorine gas was supplied at a rate of 0.33 mol/h for three hours to conduct the reaction while maintaining the reaction temperature at 50° C. After the completion of the reaction, the reaction mixture was cooled to the room temperature and analyzed with gas-chromatography. The results are recorded in Table 7.

TABLE 7

Effect of reaction time on the conversion of cumene and product yields over catalyst composite material, aluminosilicate, zeolite K-L, in the presence of 1,2-dichloroethane.

| Reaction time (h) | 0.5 | 1.0 | 2.0 | 3.0 |
|---|---|---|---|---|
| Cumeneconversion (wt. %) | 5.70 | 18.90 | 68.80 | 98.50 |
| Product yields (wt. %) | | | | |
| 2-chlorocumene | 0.17 | 0.72 | 2.85 | 6.61 |
| 3-chlorocumene | 0.00 | 0.17 | 0.81 | 0.71 |
| 4-chlorocumene | 5.55 | 18.05 | 64.51 | 89.13 |
| α-chlorocumene | 0.00 | 0.00 | 0.00 | 0.50 |
| Polychlorinated cumenes | 0.00 | 0.00 | 0.58 | 1.56 |
| selectivity to para-chlorocumene in chlorocumenes | 97.00 | 95.30 | 94.63 | 92.40 |

EXAMPLE 7

This example describes the reaction of cumene with liquid bromine to give 4-bromocumene. 10 g of cumene, 5 g of catalyst composite material, zeolite K-L and 2.14 ml bromine were mixed in a batch reactor. The reaction mixture was stirred and heated up to 70° C. After completion of the reaction, the mixture was let to cool to room temperature and analysed by gas-chromatography. The conversion of cumene and the selectivity for 4-bromocumene were found to be 10.7 wt. % and 78.8%, respectiveley.

EXAMPLE 8

This example illustrates the preparation of 4-iodocumene. 20 g cumene, 2 g of iodine monochloride and 1 g catalyst composite material, zeolite H-beta, were taken for the reaction in a three necked flask. The reaction mixture was stirred and heated up to 70° C. After the completion of the reaction, the reacation mixture was cooled to the room temperature and analyzed with gas-chromatography. The conversion of cumene and the selectivity for 4-iodocumene were found to be 7.6 wt. % and 79.6%, respectively.

The advantages of the present invention are:

(1) The resulting advantages are that a corrosion free plant can be used.
(2) A recyclable zeolite can be used.
(3) The expenditure on homogeneous Lewis acid catalysts such as $FeCl_3$ is no longer necessary.
(4) The problem of the need to dispose off inorganic byproducts does not arise.
(5) Due to the shape selectivity and porous nature of zeolites, these catalysts produce higher amount of para-products at the expence of the other consecutive products.
(6) The process of the present invention shows remarkably high industrial merits over proir art process for the preparation of halocumenes. The starting materials are easily available and easy to handle and that halocumenes can be produced in high yield by extremly simple operation.

We claim:

1. A process for the preparation of halocumenes of the formula:

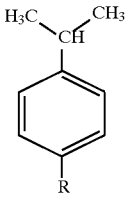

wherein R is selected from the group consisting of chlorine, bromine, and iodine, said process comprising the step of reacting cumene with a halogenating agent in a liquid phase at a temperature in the range of 5 and 150° C. at autogenous pressure for a period of 1 to 20 hours in the presence of an, aliphatic carboxylic acid and a zeolite catalyst selected from the group consisting of a K-L zeolite and an H-beta zeolite.

2. The process of claim 1 wherein said zeolite catalyst has the molar composition: $M_{2/n}O: Al_2O_3: zSiO_2$ where M is selected from the group consisting of alkali and alkaline earth metals with valency n, and wherein z is between about 2 and 500.

3. The process of claim 2 wherein the $SiO_2 : Al_2O_3$ molar ratio of said catalyst is between about 2 and 10.

4. The process of claim 3 wherein the pore size of said catalyst is about 6 to 10 angstroms.

5. The process of claim 1 wherein said liquid phase is a chlorinated solvent.

6. The process of claim 5 wherein said chlorinated solvent is selected from the group consisting of dichloromethane, 1,2-dichloroethane, 1,1,1-trichloroethane, 1,1,2,2-tetrachloroethane, and sulpholane.

7. The process of claim 6 wherein said chlorinated solvent is 1,2-dichloroethane.

8. The process of claim 1 wherein said aliphatic carboxylic acid is selected from the group consisting of acetic acid, propionic acid, isovaleric acid, mono-chloroacetic acid, mono-bromoacetic acid, dichloroacetic acid, trichloroacetic acid, alpha-chloropropionic acid, beta-chloropropionic acid, pentafluoropropionic acid, and beta-chlorotetrafluoropropionic acid.

9. The process of claim 1 wherein said aliphatic carboxylic acid is selected from the group consisting of carboxylic acid halides, carboxylic acid anhydrides, and metal salts of carboxylic acid.

10. The process of claim 1 wherein the proportion of cumene, solvent, aliphatic carboxylic acid, microporous crystalline zeolite catalyst composite material and halogenating agent used ranges from 0.01 to 1 mol., 0 to 500 ml, 0 to 50 wt. %, 0.1 to 900 g/mol cumene, and 0.001 to 500 mol/h respectively.

11. The process of claim 8, wherein the zeolite has a molar composition: $M_{2/n}O: Al_2O_3: zSiO_2$ (where M is selected from the group consisting of alkali and alkaline earth metals with valency n, and wherein z is between about 2 and 500).

12. The process of claim 1, wherein the recovering step comprises selective recovery of a 4 halocumene.

* * * * *